United States Patent
Peng et al.

(10) Patent No.: US 9,328,042 B2
(45) Date of Patent: May 3, 2016

(54) INTEGRATED PROCESS FOR THE PRODUCTION OF Z-1,1,1,4,4,4-HEXAFLUORO-2-BUTENE

(71) Applicant: THE CHEMOURS COMPANY FC, LLC, Wilmington, DE (US)

(72) Inventors: Sheng Peng, Hockessin, DE (US); Andrew Jackson, Newark, DE (US); Mario Joseph Nappa, Newark, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 14/813,383

(22) Filed: Jul. 30, 2015

(65) Prior Publication Data

US 2016/0039728 A1 Feb. 11, 2016

Related U.S. Application Data

(60) Provisional application No. 62/035,657, filed on Aug. 11, 2014.

(51) Int. Cl.
C07C 17/02 (2006.01)
C07C 17/00 (2006.01)
C07C 17/20 (2006.01)
C07C 17/04 (2006.01)
C07C 17/25 (2006.01)

(52) U.S. Cl.
CPC ............ *C07C 17/04* (2013.01); *C07C 17/25* (2013.01)

(58) Field of Classification Search
CPC ...... C07C 17/04; C07C 17/25; C07C 17/354; C07C 17/358
USPC .................. 570/151, 154, 160, 161
See application file for complete search history.

(56) References Cited

U.S. PATENT DOCUMENTS

| 6,329,560 B2 | 12/2001 | Nakada et al. | |
| 2013/0158304 A1* | 6/2013 | Quan | B01J 21/04 570/151 |
| 2015/0203423 A1* | 7/2015 | Peng | C07C 17/25 570/156 |

FOREIGN PATENT DOCUMENTS

WO 2014052695 A1 4/2014

* cited by examiner

*Primary Examiner* — Jafar Parsa
(74) *Attorney, Agent, or Firm* — Gerard E. Reinhardt

(57) ABSTRACT

The present invention provides an efficient and cost effect synthesis route from a specific starting material of 2,3-dichloro-1,3-butadiene to the desired product of Z-1,1,1,4,4,4-hexafluoro-2-butene.

15 Claims, No Drawings

INTEGRATED PROCESS FOR THE PRODUCTION OF Z-1,1,1,4,4,4-HEXAFLUORO-2-BUTENE

CROSS-REFERENCE TO RELATED APPLICATIONS

This application claims the benefit of U.S. Provisional application No. 62/035,657, filed on Aug. 11, 2014, which is incorporated in its entirety.

BACKGROUND INFORMATION

1. Field of the Disclosure

This disclosure relates to an Integrated Process for the production of Z-1,1,1,4,4,4-hexafluoro-2-butene from 2,3-dichloro-1,3-butadiene.

2. Description of the Related Art

Hexachlorobutadiene, (HCBD), is primarily produced in chlorinolysis plants as a by-product in the production of carbon tetrachloride and tetrachloroethene. Chlorinolysis is a radical chain reaction that occurs when hydrocarbons are exposed to chlorine gas under pyrolytic conditions. The hydrocarbon is chlorinated and the resulting chlorocarbons are broken down. This process is analogous to combustion, but with chlorine instead of oxygen.

Hexachlorobutadiene occurs as a heavy by-product during the chlorinolysis of butane derivatives in the production of both carbon tetrachloride and tetrachloroethene. These two commodities are manufactured on such a large scale, that enough HCBD can generally be obtained to meet industrial demand. HCBD is used domestically in China for solvent applications because of high chlorine solubility and resistance to chlorination. Methods exist wherein hexachlorobutadiene can be directly synthesized via the chlorination of butane or butadiene. Manufacturers in the United States have optimized their chlorine feedstock processes to minimize HCBD formation.

Thus, there is a need for manufacturing processes that provides halogenated hydrocarbons and fluoroolefins from a low cost and obtainable starting material.

SUMMARY

The present invention is directed to a process for the preparation of of Z-1,1,1,4,4,4-hexafluoro-2-butene from 2,3-dichloro-1,3-butadiene. The process of the present invention includes the sequential steps initiating with initiating the reaction of chlorine with 2,3-dichloro-1,3-butadiene to obtain 1,2,2,3,3,4 hexachlorobutane followed by contacting the 1,2,2,3,3,4 hexachlorobutane with tetrabutyl ammonium chloride in a basic aqueous solution to produce 1,2,3,4-tetrachlorobuta-1,3-diene. Chlorine is added to the 1,2,3,4-tetrachlorobuta-1,3-diene to obtain 1,1,2,2,3,3,4,4 octachlorabutane followed by contacting the 1,1,2,2,3,3,4,4 octachlorobutane with tetrabutyl ammonium chloride in a basic aqueous solution to produce 1,1,2,3,4,4-hexachlorobuta-1,3-diene. Hydrogen fluoride is chlorinated and combined with the 1,1,2,3,4,4-hexachlorobuta-1,3-diene to provide E- or Z-1326mxz (1,1,1,4,4,4-hexafluoro-2-chloro-2-butene). Z-1,1,1,4,4,4-hexafluoro-2-chloro-2-butene is reacted with an aqueous solution of an alkali metal hydroxide and an alkali metal halide in the presence of a quaternary alkylammonium salt having alkyl groups of from four to twelve carbon atoms and mixtures thereof, to produce a mixture including hexafluoro-2-butyne. The final step is hydrogenating hexafluoro-2-butyne to 1,1,1,4,4,4 hexafluro-2-butene.

Some of the many variations of the present invention can be described in embodiments, a series of which follows. Thus, in Embodiment 1, the invention is directed to a process for the preparation of Z-1,1,1,4,4,4-hexafluoro-2-butene from 2,3-dichloro-1,3-butadiene comprising the Steps of:

a) contacting chlorine with 2,3-dichloro-1,3-butadiene to obtain 1,2,2,3,3,4-hexachlorobutane;

b) contacting the 1,2,2,3,3,4-hexachlorobutane with a first basic aqueous solution to produce 1,2,3,4-tetrachlorobuta-1,3-diene;

c) adding chlorine to the 1,2,3,4-tetrachlorobuta-1,3-diene to obtain 1,1,2,2,3,3,4,4-octachlorabutane;

d) contacting the 1,1,2,2,3,3,4,4-octachlorobutane in a second basic aqueous solution to produce 1,1,2,3,4,4-hexachlorobuta-1,3-diene.

e) combining hydrogen fluoride with the 1,1,2,3,4,4-hexachlorobuta-1,3-diene to obtain E- and Z-1326mxz (1,1,1,4,4,4-hexafluoro-2-chloro-2-butene);

f) reacting Z-1,1,1,4,4,4-hexafluoro-2-chloro-2-butene with an aqueous solution of an alkali metal hydroxide and an alkali metal halide to produce a mixture comprising hexafluoro-2-butyne; and, g) hydrogenating hexafluoro-2-butyne to 1,1,1,4,4,4 hexafluro-2-butene.

In Embodiment 2, the invention is directed to the process according to Embodiment 1, wherein any one, any two or all three of Steps (b), (d) and (f) proceed in the presence of a phase transfer catalyst comprising an independently selected quaternary alkylammonium salt comprising alkyl groups of from four to twelve carbon atoms and mixtures thereof. In Embodiment 3, the invention is directed to the process according to Embodiment 2, wherein said phase transfer catalyst comprises tetrabutyl ammonium chloride.

In Embodiment 4, the invention is directed to the process according to Embodiment 1, wherein either or both of Steps (a) and (c) proceed in the presence of a chlorination catalyst independently selected from the group consisting of $SbCl_3$, $FeCl_3$, $CrCl_3$ and $AlCl_3$.

In Embodiment 5, the invention is directed to the process according to Embodiment 4, wherein the reaction of chlorine with 2,3-dichloro-1,3-butadiene to obtain 1,2,2,3,3,4-hexachlorobutane in Step (a) is performed at approximately 21° C.

In Embodiment 6, the invention is directed to the process according to Embodiment 2, wherein Step (b) further comprises dissolving said 1,2,2,3,3,4-hexachlorobutane and said quaternary alkylammonium salt in a dissolving solution.

In Embodiment 7, the invention is directed to the process according to Embodiment 6, wherein said dissolving solution is THF.

In Embodiment 8, the invention is directed to the process according to Embodiment 4, wherein the reaction of chlorine with 1,2,3,4-tetrachlorobuta-1,3-diene to obtain 1,1,2,2,3,3,4,4-octachlorabutane in Step (c) is performed at approximately 21° C.

In Embodiment 9, the invention is directed to the process according to Embodiment 2, wherein Step (d) further comprises dissolving said 1,1,2,2,3,3,4,4-octachlorobutane and said in a dissolving solution.

In Embodiment 10, the invention is directed to the process according to Embodiment 9, wherein said dissolving solution is THF.

In Embodiment 11, the invention is directed to the process according to Embodiment 9, wherein in the ratio of Z-versus E-1326mxz (1,1,1,4,4,4-hexafluoro-2-chloro-2-butene) in Step (e) is greater than 90%.

In Embodiment 12, the invention is directed to the process according to Embodiment 9, wherein the reaction of Step (e) is run at approximately 100° C. and 160 psig.

In Embodiment 13, the invention is directed to the process according to Embodiment 12, wherein the conversion of Z-1, 1,1,4,4,4-hexafluoro-2-chloro-2-butene to hexafluoro-2-butyne is at least 50% per hour.

In Embodiment 14, the invention is directed to the process according to Embodiment 2, wherein said alkali metal halide is sodium chloride.

In Embodiment 15, the invention is directed to the process according to Embodiment 1, The process according to claim 1, wherein said first and second basic aqueous solutions independently comprise a base selected from the group consisting of lithium hydroxide, sodium hydroxide, potassium hydroxide, calcium hydroxide, magnesium oxide, calcium oxide, sodium carbonate, potassium carbonate, sodium phosphate, potassium phosphate, and mixtures thereof.

The foregoing general description and the following detailed description are exemplary and explanatory only and are not restrictive of the invention, as defined in the appended claims.

DETAILED DESCRIPTION

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

The present invention is directed to a process for the preparation of of Z-1,1,1,4,4,4-hexafluoro-2-butene from 2,3-dichloro-1,3-butadiene. The process provides an efficient and cost effective synthesis route to the desired product of Z-1,1,1,4,4,4-hexafluoro-2-butene from a specific starting material.

Below is a schematic illustrating each step of the synthesis of 2,3-dichloro-1,3-butadiene to Z-1,1,1,4,4,4-hexafluoro-2-butene and discussion each step.

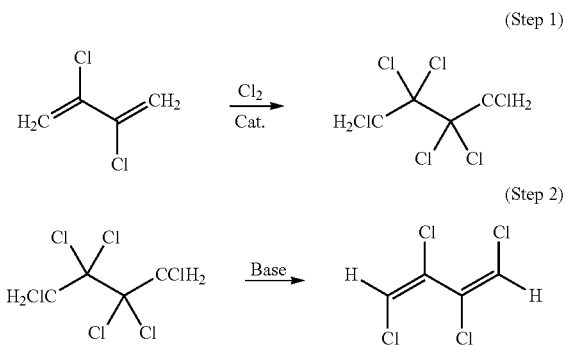

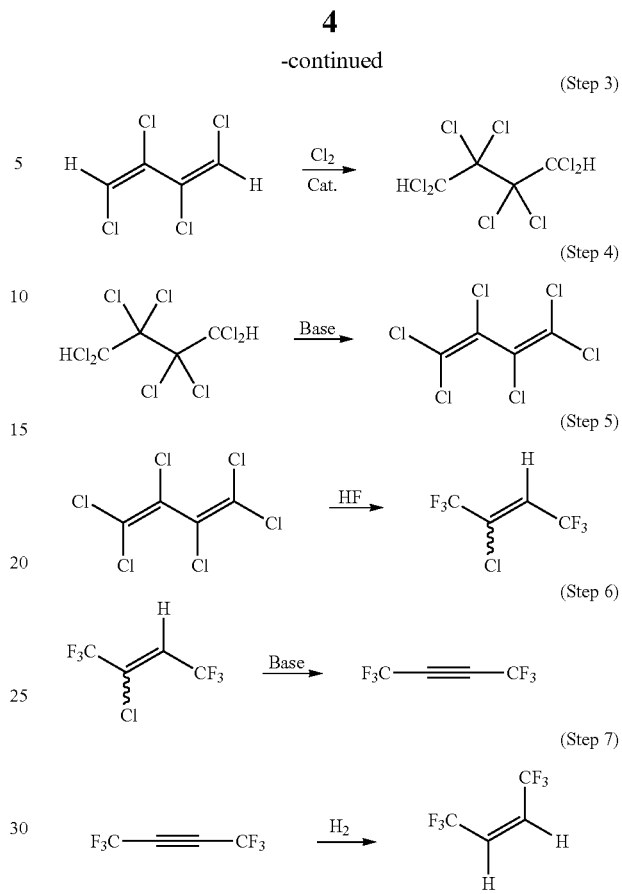

An important aspect of the invention is providing steps initiating with a specific "starting material" of 2,3-Dichloro 1,3-butadiene to obtain 1,1,2,3,4,4 hexachlorobutadiene from which point the process can continue to obtain the desired final product of Z-1,1,1,4,4,4-hexafluoro-2-butene. In existing art, commonly the starting material $CH_2Cl-C\equiv C-CH_2Cl$ is used to make hexachlorobutadiene. Such starting materials are much more expensive than the starting material of the present invention 2,3-dichloro 1,3-butadiene, commercially available from DuPont.

In the present invention, the synthesis of 2,3-dichloro 1,3-butadiene to obtain 1,1,2,3,4,4 hexachlorobutadiene proceeds in an effective and cost efficient manner in a sequential stepwise process wherein each step provides a high yield, high quality product to initiate the next steps of the process. 2,3-dichloro 1,3-butadiene can react with chlorine, from ambient temperature to 100° C., and the product can be isolated by recrystallization. The subsequent dehydrochlorination can be performed with base in the presence of a phase transfer catalyst. Chlorination of 1,2,3,4-tetrachloro-1,3-butadiene can be done at ambient temperature to elevated temperature, followed by hehydrochlorination to hexachlorobutadiene. The symmetry of Steps 1 and 3, and of Steps, 2 and 4 provide a cost effective process from a commercially available cost effective starting material to 1,1,2,3,4,4-hexachlorobutadiene, which can thereafter be processed into desired products as provided in the present invention. The inexpensive starting material and reagents, such as base and chlorine, allow the process to be efficient and cost effective. Steps (a) through (g) below correspond to Steps 1 through 7 above, respectively.

Step (a)

The process of the present invention includes sequential steps initiating with Step (a) of reacting chlorine with 2,3- dichloro-1,3-butadiene to obtain 1,2,2,3,3,4 hexachlorobutane. In a first embodiment, the reaction of chlorine with 2,3-dichloro-1,3-butadiene to obtain 1,2,2,3,3,4 hexachlorobutane is performed at an ambient temperature, approximately 21° C. A chlorination catalyst is provided for chlorination but the reaction is allowed to proceed for a defined duration. Suitable chlorination catalysts include metal trichlorides such as $SbCl_3$, $FeCl_3$, $CrCl_3$ and $AlCl_3$. The ratio of chlorine to 2,3-dichloro-1,3-butadiene is about 1.5 to 1.

Step (b)

The 1,2,2,3,3,4 hexachlorobutane is contacted with tetrabutyl ammonium chloride in a basic aqueous solution to produce 1,2,3,4-tetrachlorobuta-1,3-diene. A dissolving solution is provided for 1,2,2,3,3,4 hexachlorobutane which can include acetonitrile and tetrahydrofuran (THF). These dissolving solutions are necessary because hexachlorobutane is a solid, it is not water soluble and therefore, it does not mix well with the aqueous base. The organic solvent is used to dissolve it. A phase transfer catalyst, including but not limited to quaternary alkylammonium salt having alkyl groups of from four to twelve carbon atoms and mixtures thereof, is provided. The reaction is controlled by use of an ice bath so as to maintain the reactants to less than about 15° C.; this controls the reaction and minimizes by-product formation.

Step (c)

Chlorine is added to the 1,2,3,4-tetrachlorobuta-1,3-diene to obtain 1,1,2,2,3,3,4,4 octachlorabutane at an ambient temperature, approximately 21° C. A catalyst is provided for chlorination but the reaction is allowed to proceed for a defined duration. Suitable catalysts include metal trichlorides such as $SbCl_3$, $FeCl_3$, $CrCl_3$ and $AlCl_3$. The catalyst used in Step (c) may be the same or different from that used in Step (a). The ratio of chlorine to 2,3-dichloro-1,3-butadiene is about 1.5 to 1.

Step (d)

The 1,1,2,2,3,3,4,4 octachlorobutane is contacted with tetrabutyl ammonium chloride in a basic aqueous solution to produce 1,1,2,3,4,4-hexachlorobuta-1,3-diene at a ratio of about 2.5 to 1. A dissolving solution is provided which can include acetonitrile and THF. A phase transfer catalyst including but not limited to quaternary alkylammonium salt having alkyl groups, of from four to twelve carbon atoms and mixtures thereof, is provided. An ice bath to maintain the reactants to less than about 15° C. is provided.

Step (e)

Hydrogen fluoride is chlorinated and combined with the 1,1,2,3,4,4-hexachlorobuta-1,3-diene to provide E- or Z-1326mxz (1,1,1,4,4,4-hexafluoro-2-chloro-2-butene). A general procedure for this reaction was disclosed in U.S. Pat. No. 6,329,560 to Nakada et al.; incorporated herein in relevant part. This process predominately provides Z-1326 with a selectivity of greater than 90%.

Step (f)

Z-1,1,1,4,4,4-hexafluoro-2-chloro-2-butene is reacted with an aqueous solution of an alkali metal hydroxide and an alkali metal halide in the presence of a quaternary alkylammonium salt having alkyl groups, of from four to twelve carbon atoms and mixtures thereof, to produce a mixture including hexafluoro-2-butyne.

Step (g)

The final step is hydrogenating hexafluoro-2-butyne to 1,1,1,4,4,4 hexafluro-2-butene.

The process for producing hexafluoro-2-butyne by reacting Z-1,1,1,4,4,4-hexafluoro-2-chloro-2-butene (HCFC-1326mxz) with an aqueous solution of an alkali metal hydroxide in the presence of a quaternary alkylammonium salt, having alkyl groups of from four to twelve carbon atoms, is detailed in PCT/US2013/062080 (WO2014052695) which is incorporated herein in relevant part. The product and mixtures thereof produce and recover a mixture including hexafluoro-2-butyne, wherein the conversion of Z-1,1,1,4,4,4-hexafluoro-2-chloro-2-butene to hexafluoro-2-butyne is at least 50% per hour.

As used herein, phase transfer catalyst is intended to mean a substance that facilitates the transfer of ionic compounds into an organic phase from an aqueous phase or from a solid phase. The phase transfer catalyst facilitates the reaction of these dissimilar and incompatible components. While various phase transfer catalysts may function in different ways, their mechanism of action is not determinative of their utility in the present invention provided that the phase transfer catalyst facilitates the dehydrochlorination reaction.

A phase transfer catalyst as used herein is a quaternary alkylammonium salt wherein the alkyl groups are alkyl chains having from four to twelve carbon atoms. Potentially the quaternary alkyl ammonium salt is a tetrabutylammonium salt. The anions of the salt can be halides such as chloride or bromide, hydrogen sulfate, or any other commonly used anion.

The Z- and E-isomers of 1,1,1,4,4,4-hexafluoro-2-chloro-2-butene exhibit significantly different reactivity with respect to dehydrochlorination. In the present invention, the process produces mainly the Z isomer. Dehydrochlorination of the Z-isomer $CF_3CCl=CHCF_3$ can be effected with quaternary alkylammonium salts wherein the alkyl groups are alkyl chains having from four to twelve carbon atoms. The anions of the salt can be halides such as chloride or bromide, hydrogen sulfate, or any other commonly used anion. As used herein, the basic aqueous solution is a liquid (whether a solution, dispersion, emulsion, or suspension and the like) that is primarily an aqueous liquid having a pH of over 7. Thus, the only pH limitation is that it is not in the acidic range.

In some embodiments, the basic aqueous solution contains small amounts of organic liquids which may be miscible or immiscible with water. In some embodiments, the liquid medium in the basic aqueous solution is at least 90% water. In one embodiment the water is tap water; in other embodiments the water is deionized or distilled. One skilled in the art will appreciate this process is a method for the synthesis of Z-1,1,1,4,4,4 hexafluro-2-butene (Z-HFO-1326mxz) from hexafluoro-2-butyne in high selectivity by selective hydrogenation in the presence of particular catalysts.

In the foregoing specification, and more particularly in Step (f) and (g), the concepts have been described with reference to specific embodiments. However, one of ordinary skill in the art appreciates that various modifications and changes can be made without departing from the scope of the invention. It will be understood that variations in the conditions of the reactions are appreciated based on an understanding of the conditions and devices used. For example, the contact time in the reaction zone is reduced by increasing the flow rate of fluorinated alkyne and hydrogen into the reaction zone. As the flow rate is increased this will increase the amount of fluorinated alkyne being hydrogenated per unit time. Since the hydrogenation is exothermic, depending on the length and diameter of the reaction zone, and its ability to dissipate heat, at higher flow rates it may be desirable to provide a source of external cooling to the reaction zone to maintain a desired temperature.

Other features and benefits of any one or more of the embodiments will be apparent from the following examples, and from the claims.

EXAMPLES

The concepts described herein will be further described in the following examples, which do not limit the scope of the invention described in the claims.

Example Step (a)

$Cl_2$ is added slowly to 2,3-dichloro 1,3-butadiene (123 g, 1 mol) in 1 L of 0014 in the presence of SbCl3 (12.3 g) at room temperature. The reaction is proceeded for 2-4 hours, and the 1,2,2,3,3,4-hexachlorobutane is obtained as a colorless solid (200 g, 75.5%) after 0014 removal, m.p. 105° C.

Example Step (b)

30% NaOH aqueous solution is (107 g, 0.8 mol) is added dropwise to 1,2,2,3,3,4-hexachlorobutane (132.5 g, 0.5 mol) in a 1:1 mixture of THF and water in the presence of tetrabutyl ammonium chloride, and an ice bath is used to control the temperature below 15° C. Upon the completion of the reaction, THF is removed, the product 1,2,3,4-tetrachlorobuta-1,3-diene (30.7 g, 40%) is collected as a mixture of colorless oil and white solid.

Example Step (c)

$Cl_2$ is added slowly to 1,2,3,4-tetrachlorobuta-1,3-diene (96 g, 0.5 mol) in 500 mL of $CCl_4$ in the presence of $SbCl_3$ (9.6 g) at room temperature. The reaction is proceeded for 2-4 hours, and the 1,1,2,2,3,3,4,4-octachlorobutane is obtained as a colorless solid (100 g, 60%) after $CCl_4$ removal. m.p. 80° C.

Example Step (d)

30% NaOH aqueous solution is (40 g, 0.3 mol) is added dropwise to 1,2,2,3,3,4-hexachlorobutane (83.5, 0.25 mol) in a 1:1 mixture of THF and water in the presence of tetrabutyl ammonium chloride, and an ice bath is used to control the temperature below 15° C. Upon the completion of the reaction, THF is removed, the product 1,2,3,4-tetrachlorobuta-1,3-diene (32 g, 50%) is collected as a colorless oil.

Example (1)

Step (e)

$SbCl_5$ (10.5 g) was added into a 210 mL Hastelloy® C reactor, followed by HF addition (49 g). The reaction mixture was heated to 110° C. for 1 hour and cooled to 0° C. Hexachlorobutadiene (30 g) was added to the reactor and the reaction was heated back to 110° C. for 20 hours. 50 g ice water was added to quench the reaction. Phase separation of the product ensued. GC showed 100% conversion of the starting material and 95% selectivity to the desired 1326mxz.

Example (2)

Step (e)

$TaCl_5$ (12.53 g) was added into a 210 mL Hastelloy® C reactor, followed by HF addition (49 g). The reaction mixture was heated to 150° C. for 1 hour and cooled to 0° C. Hexachlorobutadiene (30 g) was added to the reactor and the reaction was heated back to 120° C. for 20 hours. 50 g ice water was added to quench the reaction. Phase separation of the product ensued. GC showed 50% conversion of the starting material and 91.7% selectivity to the desired 1326mxz.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process for the preparation of Z-1,1,1,4,4,4-hexafluoro-2-butene from 2,3-dichloro-1,3-butadiene comprising the Steps of:
    a) contacting chlorine with 2,3-dichloro-1,3-butadiene to obtain 1,2,2,3,3,4-hexachlorobutane;
    b) contacting the 1,2,2,3,3,4-hexachlorobutane with a first basic aqueous solution to produce 1,2,3,4-tetrachlorobuta-1,3-diene;
    c) adding chlorine to the 1,2,3,4-tetrachlorobuta-1,3-diene to obtain 1,1,2,2,3,3,4,4-octachlorabutane;
    d) contacting the 1,1,2,2,3,3,4,4-octachlorobutane in a second basic aqueous solution to produce 1,1,2,3,4,4-hexachlorobuta-1,3-diene.
    e) combining hydrogen fluoride with the 1,1,2,3,4,4-hexachlorobuta-1,3-diene to obtain E- and Z-1326mxz (1,1,1,4,4,4-hexafluoro-2-chloro-2-butene);
    f) reacting Z-1,1,1,4,4,4-hexafluoro-2-chloro-2-butene with an aqueous solution of an alkali metal hydroxide and an alkali metal halide to produce a mixture comprising hexafluoro-2-butyne; and,
    g) hydrogenating hexafluoro-2-butyne to 1,1,1,4,4,4 hexafluro-2-butene.

2. The process according to claim 1, wherein any one, any two or all three of Steps (b), (d) and (f) proceed in the presence of a phase transfer catalyst comprising an independently selected quaternary alkylammonium salt comprising alkyl groups of from four to twelve carbon atoms and mixtures thereof.

3. The process according to claim 2, wherein said phase transfer catalyst comprises tetrabutyl ammonium chloride.

4. The process according to claim 1, wherein either or both of Steps (a) and (c) proceed in the presence of a chlorination catalyst independently selected from the group consisting of $SbCl_3$, $FeCl_3$, $CrCl_3$ and $AlCl_3$.

5. The process according to claim 4, wherein the reaction of chlorine with 2,3-dichloro-1,3-butadiene to obtain 1,2,2,3,3,4-hexachlorobutane in Step (a) is performed at approximately 21° C.

6. The process according to claim 2, wherein Step (b) further comprises dissolving said 1,2,2,3,3,4-hexachlorobutane and said quaternary alkylammonium salt in a dissolving solution.

7. The process according to claim 6, wherein said dissolving solution is THF.

8. The process according to claim 4, wherein the reaction of chlorine with 1,2,3,4-tetrachlorobuta-1,3-diene to obtain 1,1,2,2,3,3,4,4-octachlorabutane in Step (c) is performed at approximately 21° C.

9. The process according to claim 2, wherein Step (d) further comprises dissolving said 1,1,2,2,3,3,4,4-octachlorobutane and said in a dissolving solution.

10. The process according to claim 9, wherein said dissolving solution is THF.

11. The process according to claim 9, wherein in the ratio of Z-versus E-1326mxz (1,1,1,4,4,4-hexafluoro-2-chloro-2-butene) in Step (e) is greater than 90%.

12. The process according to claim 9, wherein the reaction of Step (e) is run at approximately 100° C. and 160 psig.

13. The process according to claim 12, wherein the conversion of Z-1,1,1,4,4,4-hexafluoro-2-chloro-2-butene to hexafluoro-2-butyne is at least 50% per hour.

14. The process according to claim 2, wherein said alkali metal halide is sodium chloride.

15. The process according to claim 1, wherein said first and second basic aqueous solutions independently comprise a base selected from the group consisting of lithium hydroxide, sodium hydroxide, potassium hydroxide, calcium hydroxide, magnesium oxide, calcium oxide, sodium carbonate, potassium carbonate, sodium phosphate, potassium phosphate, and mixtures thereof.

* * * * *